(12) United States Patent
Mutz

(10) Patent No.: US 8,592,440 B2
(45) Date of Patent: *Nov. 26, 2013

(54) CRYSTALLINE FORM I OF IMATINIB MESYLATE

(75) Inventor: Michael Mutz, Freiburg i.Br. (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/183,572

(22) Filed: Jul. 15, 2011

(65) Prior Publication Data

US 2012/0015955 A1 Jan. 19, 2012

Related U.S. Application Data

(62) Division of application No. 13/006,505, filed on Jan. 14, 2011, now Pat. No. 8,198,289, which is a division of application No. 12/094,629, filed as application No. PCT/EP2006/011240 on Nov. 23, 2006, now Pat. No. 7,893,076.

(60) Provisional application No. 60/740,016, filed on Nov. 28, 2005, provisional application No. 60/740,017, filed on Nov. 28, 2005, provisional application No. 60/740,018, filed on Nov. 28, 2005.

(30) Foreign Application Priority Data

Nov. 25, 2005 (GB) .................................... 0524061.9
Nov. 25, 2005 (GB) .................................... 0524062.7

(51) Int. Cl.
*A61K 31/505* (2006.01)

(52) U.S. Cl.
USPC ........... 514/275; 424/452; 544/331; 544/360; 546/268.1

(58) Field of Classification Search
USPC .................. 424/452; 514/275; 544/331, 360; 546/268.1
See application file for complete search history.

(56) References Cited

U.S. PATENT DOCUMENTS 6,894,051 B1   5/2005  Zimmermann et al.
2005/0234069 A1*  10/2005  Parthasaradhi et al. .. 514/252.18

FOREIGN PATENT DOCUMENTS

| WO | WO 99/03854 | 1/1999 |
|---|---|---|
| WO | WO 2004/106326 | 9/2004 |
| WO | WO2005/075454 | 8/2005 |
| WO | WO 2005/077933 | 8/2005 |
| WO | WO 2005/095379 | 10/2005 |
| WO | WO2005/117885 | 12/2005 |
| WO | WO 2006/024863 | 3/2006 |
| WO | WO 2006/048890 | 5/2006 |
| WO | WO 2006/054314 | 5/2006 |
| WO | WO2006/128675 | 12/2006 |
| WO | WO 2007/023182 | 3/2007 |

OTHER PUBLICATIONS

Chilean Patent Application No. 1692/1998 (Novartis AG); Equivalent to US 6,894,051 dated May 17, 2005.
Chilean Patent Application No. 209/2005 (Novartis AG); Equivalent to WO2005/075454 dated Aug. 18, 2005.
Chilean Patent Application No. 1355/2005 (Bioniche Life Sciences Inc); Equivalent to WO2005/117885 dated Dec. 15, 2005.
Chilean Patent Application No. 1082/2006 (Novartis AG); Equivalent to WO2006/128675 dated Dec. 7, 2006.
Caira, M.R., "Chrystalline polymorphism of organic compounds", Topics in Current Chemistry, Springer, vol. 198, pp. 163-208, 1998.
Nager et al., "Crystal Structures of the kinase domain of c-Abl in complex with the small molecule inhibitors PD173955 and imatinib (STI-571)", Cancer Res., vol. 65, No. 15, pp. 4236-4243, (Aug. 1, 2002).
Buchdunger et al., "Inhibition of the Abl Protein-Tyrosine Kinase in Vitro and in Vivo by a 2-Phenylaminipyrimidine Derivatives", Cancer Research, pp. 100-104, Jan. 1, 1996.
Byrn et al., "Pharmaceutical Solids: A Strategic Approach to Regulatory Considerations", Pharmaceutical Research, vol. 12, No. 7, pp. 945-954 (1995).
Davey et al., "Polymorphism in Molecular Crystals: Stabilization of a Metastable Form by Confirmation Mimicry", J. Am. Chem. Soc. vol. 119, pp. 1767-1772, 1997.
Mol et al., "Structural insights into the conformational selectivity of STI-571 and related kinase inhibitors", Current Opinion in Drug Discovery & Development, vol. 7, No. 5, pp. 639-648, 2004. Review CD.
Okano, Teisuke, "Shin-Yakuzaigaku Souron (revised 3rd edition)", Nankodo, Apr. 10, 1987, 26, 111, pp. 256-257.
IC.G. Wermuth, "Saishin Souyaku Kagaku (last volume)", Technomics, Sep. 25, 1999, pp. 452-453.

* cited by examiner

*Primary Examiner* — Douglas M Willis
(74) *Attorney, Agent, or Firm* — Stephen Johnson

(57) ABSTRACT

Crystalline forms of imatinib mesylate (F, G, H, I and K) and their respective characterizations are disclosed.

7 Claims, 5 Drawing Sheets

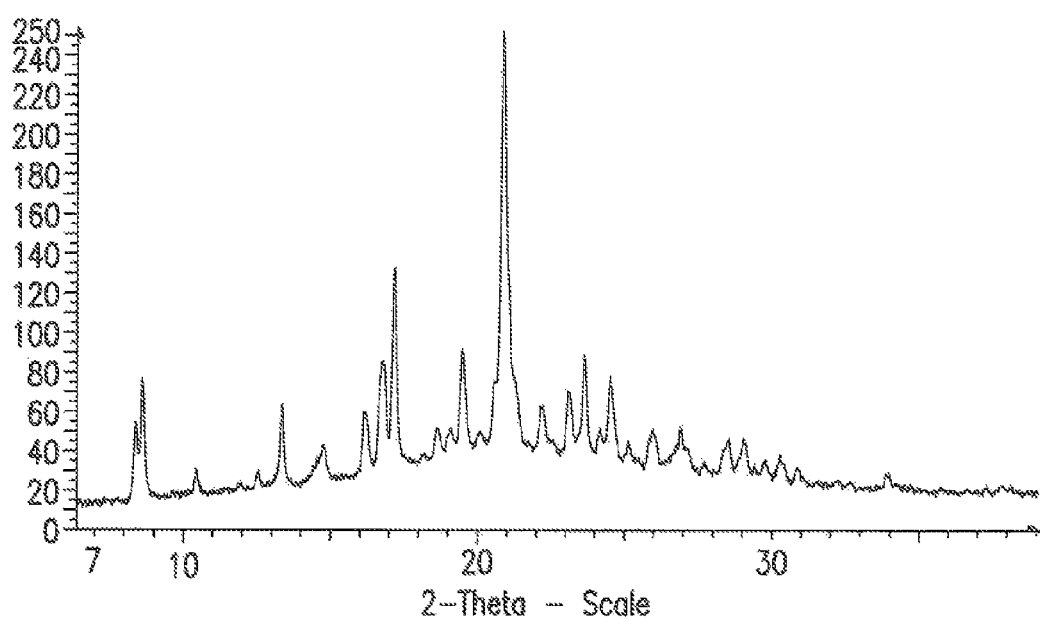
FIG. 1 (F form)

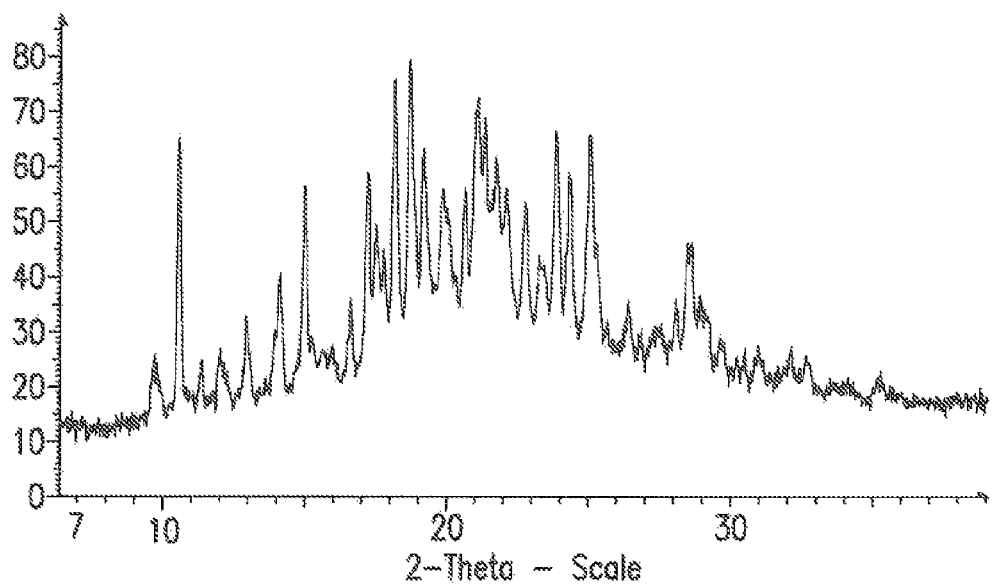
FIG. 2 (G form)

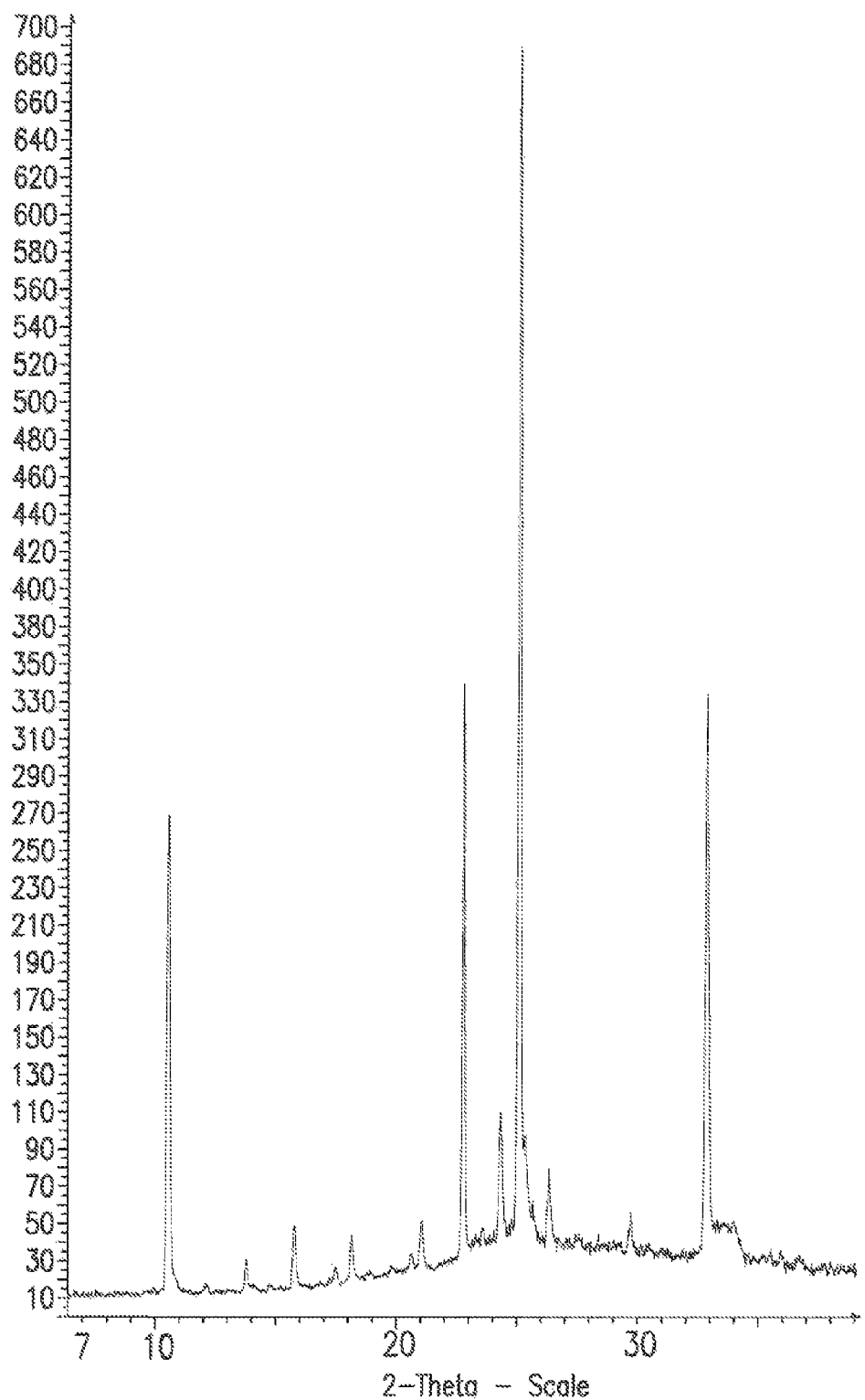
FIG.3 (H form)

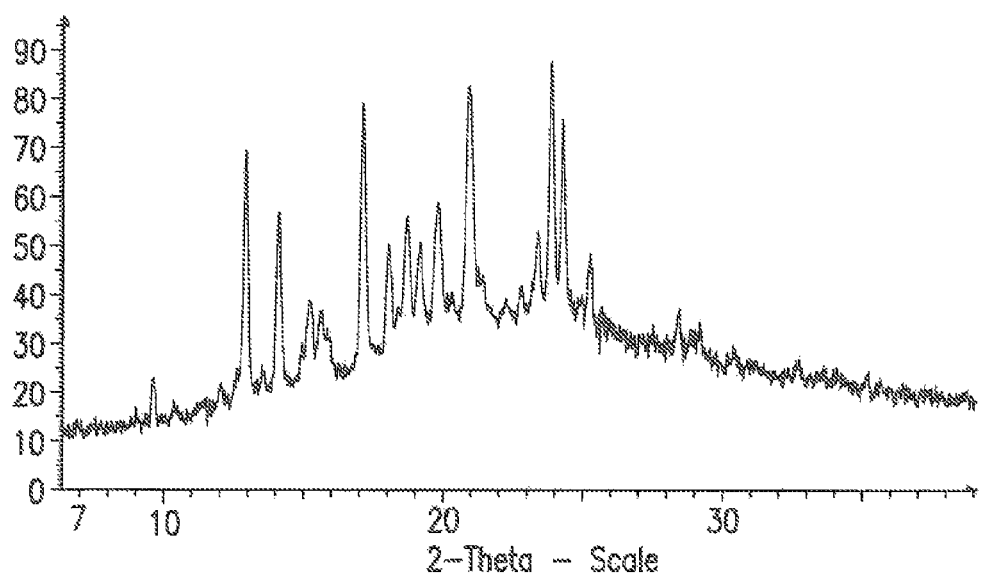
FIG. 4 (I form)

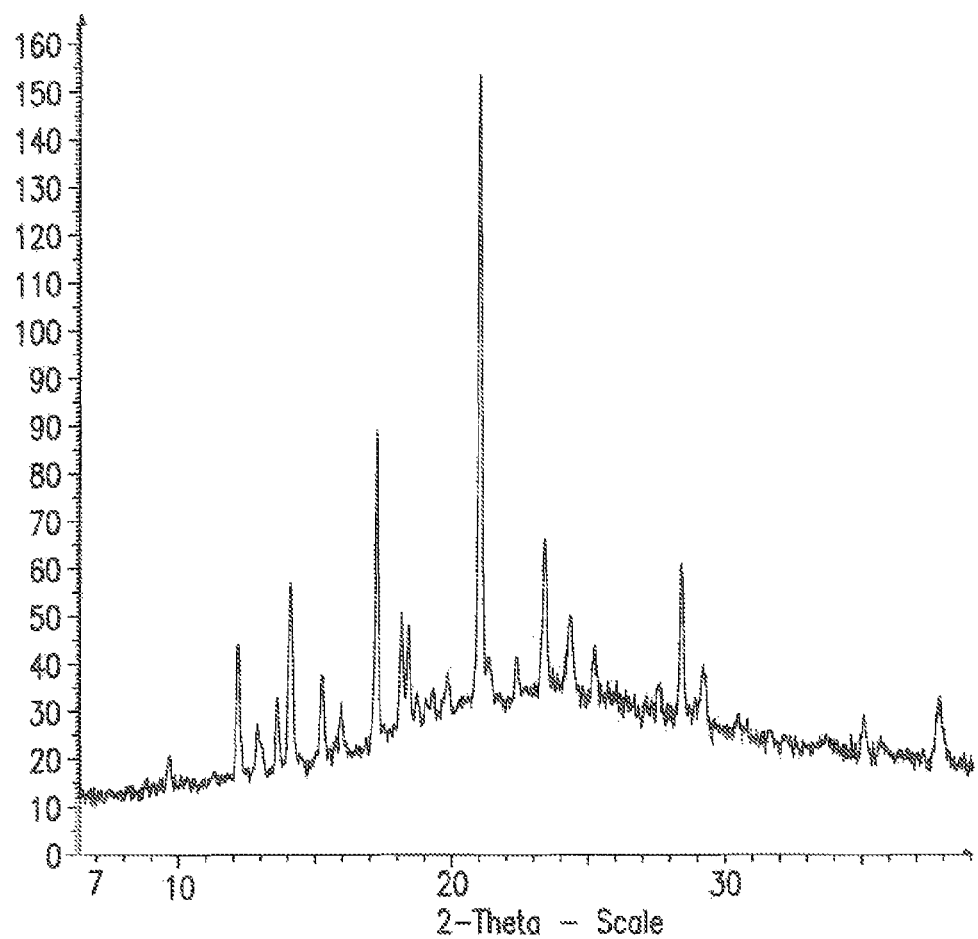
FIG.5 (K form)

CRYSTALLINE FORM I OF IMATINIB MESYLATE

CROSS-REFERENCE TO RELATED APPLICATION

This application is a divisional application of U.S. patent application Ser. No. 13/006,505, filed Jan. 14, 2011, now U.S. Pat. No. 8,189,289, which is a divisional application of U.S. patent application Ser. No. 12/094,629, filed May 22, 2008, now U.S. Pat. No. 7,893,076, which is a 35 U.S.C. §371 National Stage Filing of International Pat. Application No. PCT/EP2006/011240 filed Nov. 23, 2006, which claims priority under 35 U.S.C. §119(e) to U.S. prov. Pat. Application Nos. a) 60/740,016, filed Nov. 28, 2005, b) 60/740,017, filed Nov. 28, 2005 and c) 60/740,018, filed Nov. 28, 2005 and under 35 U.S.C. §119(a-d) to Great Britain Pat. Appl. Nos. a) GB 0524061.9, filed Nov. 25, 2005 and b) GB 0524062.7, filed Nov. 25, 2005, the entire disclosures of which are hereby incorporated by reference.

The invention relates to particular crystal forms of the methanesulfonic acid addition salt of 4-(4-methylpiperazin-1-ylmethyl)-N-[4-methyl-3-(4-(pyridin-3-yl)pyrimidin-2-ylamino)phenyl]-benzamide (the compound of formula I, see below), certain processes for their preparation, pharmaceutical compositions containing these crystal forms, and their use in diagnostic methods or, preferably, for the therapeutic treatment of warm-blooded animals, especially humans, and their use as an intermediate or for the preparation of pharmaceutical preparations for use in diagnostic methods or, preferably, for the therapeutic treatment of warm-blooded animals, especially humans.

BACKGROUND OF THE INVENTION

The preparation of 4-(4-methylpiperazin-1-ylmethyl)-N-[4-methyl-3-(4-(pyridin-3-yl)pyrimidin-2-ylamino)phenyl]-benzamide, also known as Imatinib, and its use, especially as an anti-tumour agent, are described in Example 21 of EP-A-0 564 409, which was published on 6 Oct. 1993, and in equivalent applications in numerous other countries. The compound is exemplified in these publications only in free form (not as a salt).

4-(4-Methylpiperazin-1-ylmethyl)-N-[4-methyl-3-(4-(pyridin-3-yl)pyrimidin-2-ylamino)phenyl]-benzamide mesylate, also known as Imatinib mesylate or STI571, the alpha and the beta crystal form thereof, as well as its pharmaceutical use are described in U.S. Pat. No. 6,894,051. Imatinib mesylate is the active ingredient of the drug Gleevec® (Glivec®) which is an approved medicament for the treatment of Chronic Myeloid Leukemia (CML) and gastrointestinal stromal tumors (GIST). Another polymorph of Imatinib mesylate, the so-called H1-form, is described in WO2004/106326.

It has now been surprisingly found that under certain conditions new crystal forms of the methanesulfonate salt may be found, which are described hereinafter as F-crystal form, G-crystal form, H-crystal form, I-crystal form and K-crystal form and which forms have advantageous utilities and properties.

BRIEF DESCRIPTION OF THE INVENTION

The invention is described in more detail in the following with the help of drawings and other aids.

The invention relates especially to essentially pure crystal forms, preferably those which are referred to hereinafter as the F-crystal form, G-crystal form, H-crystal form, I-crystal form and K-crystal form of the methanesulfonic acid addition salt of Imatinib of formula I,

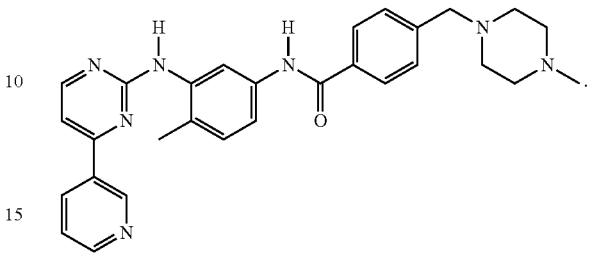

(I)

BRIEF DESCRIPTION OF THE DRAWINGS

The F-crystal form of the methanesulfonic acid addition salt of a compound of formula I is characterized by lines in the X-ray diffraction diagram observed at an angle of refraction 2theta of 8.4° and 8.6°.

FIG. 1 shows the X-ray diffraction diagram of the F-crystal form of the methanesulfonic acid addition salt of a compound of formula I. In the X-ray diagram, the angle of refraction 2theta is plotted on the horizontal axis (x-axis) and the relative line intensity (background-corrected peak intensity) on the vertical (y-axis). X-ray powder diffraction patterns are measured on a Bruker D8 GADDS Discover Diffractometer with Cu Kα radiation source (Kα1 radiation, wavelength λ=1.54060 Ångström). The optical density of the lines on the film is proportional to the light intensity. The film is scanned in using a line scanner. The strongest line in the X-ray diffraction diagram is observed at an angle of refraction 2theta of 20.9°. More broadly, the F-crystal form is characterized by refractions at angles of refraction 2theta of 8.4°, 8.6°, 13.3°, 16.2°, 16.8°, 17.1°, 19.5°, 20.9°, 23.6° and 24.5°. In essentially pure material of the F-crystal form of the methanesulfonic acid addition salt of a compound of formula I, lines can be observed at angles of refraction 2theta 8.4°, 8.6°, 10.4°, 13.3,° 14.7°, 16.2°, 16.8°, 17.1°, 19.5°, 20.9°, 22.2°, 23.1°, 23.6°, 24.5°, 25.1°, 26.0°, 26.9°, 28.5°, 29.1° and 30.3°.

The G-crystal form of the methanesulfonic acid addition salt of a compound of formula I is characterized by a line in the X-ray diffraction diagram observed at an angle of refraction 2theta of 10.5° together with the absence of any lines between an angle of refraction 2theta of 4° and 8°.

FIG. 2 shows the X-ray diffraction diagram of the G-crystal form of the methanesulfonic acid addition salt of a compound of formula I. In the X-ray diagram, the angle of refraction 2theta is plotted on the horizontal axis (x-axis) and the relative line Intensity (background-corrected peak intensity) on the vertical (y-axis). X-ray powder diffraction patterns are measured on a Bruker D8 GADDS Discover Diffractometer with Cu Kα radiation source (Kα1 radiation, wavelength λ=1.54060 Ångström). The optical density of the lines on the film is proportional to the light intensity. The film is scanned in using a line scanner. In the X-ray diffraction diagram of the G-crystal form lines are observed at an angle of refraction 2theta of 10.5°, 18.1° and 18.7°. More broadly, the G-crystal form is characterized by refractions at angles of refraction 2theta of 10.5°, 15.0°, 17.2°, 18.1°, 18.7°, 19.2°, 21.1° and 21.3°. In essentially pure material of the G-crystal form of the methanesulfonic acid addition salt of a compound of formula I, lines can be observed at angles of refraction 2theta 10.5°, 12.9°, 13.9°, 14.1°, 15.0°, 16.6°, 17.2°, 17.5°, 18.1°, 18.7°, 19.2°, 19.8°, 20.6°, 21.1°, 21.3°, 21.7°, 22.1°, 22.8°, 23.9°, 24.3°, 25.1° and 28.6°.

The H-crystal form of the methanesulfonic acid addition salt of a compound of formula I is characterized by a line in the X-ray diffraction diagram observed at an angle of refraction 2theta of 32.9°.

FIG. 3 shows the X-ray diffraction diagram of the H-crystal form of the methanesulfonic acid addition salt of a compound of formula I. In the X-ray diagram, the angle of refraction 2theta is plotted on the horizontal axis (x-axis) and the relative line intensity (background-corrected peak intensity) on the vertical (y-axis). X-ray powder diffraction patterns are measured on a Bruker D8 GADDS Discover Diffractometer with Cu Kα radiation source (Kα1 radiation, wavelength λ=1.54060 Ångström). The optical density of the lines on the film is proportional to the light intensity. The film is scanned in using a line scanner. In the X-ray diffraction diagram the H-crystal form is dominated by a line at an angle of refraction 2theta of 25.1°. More broadly, the H-crystal form is characterized by refractions at angles of refraction 2theta of 10.5°, 22.8°, 25.1° and 32.9°. In essentially pure material of the H-crystal form of the methanesulfonic acid addition salt of a compound of formula I, lines can be observed at angles of refraction 2theta 10.5°, 13.8°, 15.7°, 18.1°, 21.0°, 22.8°, 24.3°, 25.1°, 26.3°, 29.7° and 32.9°.

The I-crystal form of the methanesulfonic acid addition salt of a compound of formula I is characterized by a line in the X-ray diffraction diagram observed at an angle of refraction 2theta of 12.9° together with the absence of any lines at an angle of refraction 2theta below 9° and above 29°.

FIG. 4 shows the X-ray diffraction diagram of the I-crystal form of the methanesulfonic acid addition salt of a compound of formula I. In the X-ray diagram, the angle of refraction 2theta is plotted on the horizontal axis (x-axis) and the relative line intensity (background-corrected peak intensity) on the vertical (y-axis). X-ray powder diffraction patterns are measured on a Bruker D8 GADDS Discover Diffractometer with Cu Kα radiation source (Kα1 radiation, wavelength λ=1.54060 Ångström). The optical density of the lines on the film is proportional to the light intensity. The film is scanned in using a line scanner. In the X-ray diffraction diagram of the I-crystal form lines are observed at an angle of refraction 2theta of 12.9°, 17.1°, 20.9°, 23.9° and 24.3°. More broadly, the I-crystal form is characterized by refractions at angles of refraction 2theta of 12.9°, 14.1°, 17.1°, 18.0°, 18.7°, 19.1°, 19.8°, 20.9°, 23.9°, 24.3° and 25.2°. In essentially pure material of the I-crystal form of the methanesulfonic acid addition salt of a compound of formula I, lines can be observed at angles of refraction 2theta 9.6°, 12.9°, 14.1°, 15.2°, 15.6°, 17.1°, 18.0°, 18.7°, 19.1°, 19.8°, 20.9°, 23.4°, 23.9°, 24.3°, 25.2° and 28.4°.

The K-crystal form of the methanesulfonic acid addition salt of a compound of formula I is characterized by a line in the X-ray diffraction diagram observed at an angle of refraction 2theta of 37.9°.

FIG. 5 shows the X-ray diffraction diagram of the K-crystal form of the methanesulfonic acid addition salt of a compound of formula I. In the X-ray diagram, the angle of refraction 2theta is plotted on the horizontal axis (x-axis) and the relative line intensity (background-corrected peak intensity) on the vertical (y-axis). X-ray powder diffraction patterns are measured on a Bruker D8 GADDS Discover Diffractometer with Cu Kα radiation source (Kα1 radiation, wavelength λ=1.54060 Ångström). The optical density of the lines on the film is proportional to the light intensity. The film is scanned in using a line scanner. In the X-ray diffraction diagram the K-crystal form is further characterized by a line at an angle of refraction 2theta of 21.0°. More broadly, the K-crystal form is characterized by refractions at angles of refraction 2theta of 12.1°, 14.1°, 18.2°, 18.4°, 21.0°, 23.4° and 28.4°. In essentially pure material of the K-crystal form of the methanesulfonic acid addition salt of a compound of formula I, lines can be observed at angles of refraction 2theta 12.1°, 12.9°, 13.6°, 14.1°, 15.2°, 17.2°, 18.2°, 18.4°, 19.8°, 21.0°, 22.4°, 23.4°, 24.3°, 25.2°, 28.4°, 29.2° and 37.9°.

DETAILED DESCRIPTION OF THE INVENTION

The term "essentially pure" is understood in the context of the present invention to mean especially that at least 90, preferably at least 95, and most preferably at least 99 percent by weight of the crystals of an acid addition salt of formula I are present in the specified crystal form according to the invention.

In the context with stating that the F-crystal form of the methanesulfonic acid addition salt of a compound of formula I exhibits an X-ray diffraction diagram essentially as in FIG. 1, the term "essentially" means that at least the major lines of the diagram depicted in FIG. 1, i.e. those having a relative line intensity of more than 20%, especially more than 30%, as compared to the most intense line in the diagram, have to be present.

Alternatively, the F-crystal form of the methanesulfonic acid addition salt of a compound of formula I is characterized by a DSC curve showing a melting event at 95° C. followed by an exothermic recrystallization and a second melting at about 223° C.

In one preferred embodiment, the essentially pure methanesulfonic acid addition salt of a compound of formula I in the F-crystal form shows the X-ray diffraction diagram indicated in FIG. 1.

High preference is also given for the F-crystal form of the methanesulfonic acid addition salt of a compound of formula I which shows an X-ray diffraction diagram of the type shown in FIG. 1, in which the relative peak intensities of each peak do not deviate by more than 10% from the relative peak intensities in the diagram shown in FIG. 1, especially an X-ray diffraction diagram identical to that shown in FIG. 1.

In the context with stating that the G-crystal form of the methanesulfonic acid addition salt of a compound of formula I exhibits an X-ray diffraction diagram essentially as in FIG. 2, the term "essentially" means that at least the major lines of the diagram depicted in FIG. 2, i.e. those having a relative line intensity of more than 20%, especially more than 30%, as compared to the most intense line in the diagram, have to be present.

In one preferred embodiment, the essentially pure methanesulfonic acid addition salt of a compound of formula I in the G-crystal form shows the X-ray diffraction diagram indicated in FIG. 2.

High preference is also given for the G-crystal form of the methanesulfonic acid addition salt of a compound of formula I which shows an X-ray diffraction diagram of the type shown in FIG. 2, in which the relative peak intensities of each peak do not deviate by more than 10% from the relative peak intensities in the diagram shown in FIG. 2, especially an X-ray diffraction diagram identical to that shown in FIG. 2.

In the context with stating that the H-crystal form of the methanesulfonic acid addition salt of a compound of formula I exhibits an X-ray diffraction diagram essentially as in FIG. 3, the term "essentially" means that at least the major lines of the diagram depicted in FIG. 3, i.e. those having a relative line intensity of more than 20%, especially more than 30%, as compared to the most intense line in the diagram, have to be present.

In another preferred embodiment, the essentially pure methanesulfonic acid addition salt of a compound of formula I in the H-crystal form shows the X-ray diffraction diagram indicated in FIG. 3.

High preference is also given for the H-crystal form of the methanesulfonic acid addition salt of a compound of formula I which shows an X-ray diffraction diagram of the type shown in FIG. 3, in which the relative peak intensities of each peak do not deviate by more than 10% from the relative peak intensities in the diagram shown in FIG. 3, especially an X-ray diffraction diagram identical to that shown in FIG. 3.

In the context with stating that the I-crystal form of the methanesulfonic acid addition salt of a compound of formula I exhibits an X-ray diffraction diagram essentially as in FIG. 4, the term "essentially" means that at least the major lines of the diagram depicted in FIG. 4, i.e. those having a relative line intensity of more than 20%, especially more than 30%, as compared to the most intense line in the diagram, have to be present.

In a further preferred embodiment, the essentially pure methanesulfonic acid addition salt of a compound of formula I in the I-crystal form shows the X-ray diffraction diagram indicated in FIG. 4.

High preference is also given for the I-crystal form of the methanesulfonic acid addition salt of a compound of formula I which shows an X-ray diffraction diagram of the type shown in FIG. 4, in which the relative peak intensities of each peak do not deviate by more than 10% from the relative peak intensities in the diagram shown in FIG. 4, especially an X-ray diffraction diagram identical to that shown in FIG. 4.

In the context with stating that the K-crystal form of the methanesulfonic acid addition salt of a compound of formula I exhibits an X-ray diffraction diagram essentially as in FIG. 5, the term "essentially" means that at least the major lines of the diagram depicted in FIG. 5, i.e. those having a relative line intensity of more than 20%, especially more than 30%, as compared to the most intense line in the diagram, have to be present.

In another preferred embodiment, the essentially pure methanesulfonic acid addition salt of a compound of formula I in the K-crystal form shows the X-ray diffraction diagram indicated in FIG. 5.

High preference is also given for the K-crystal form of the methanesulfonic acid addition salt of a compound of formula I which shows an X-ray diffraction diagram of the type shown in FIG. 5, in which the relative peak intensities of each peak do not deviate by more than 10% from the relative peak intensities in the diagram shown in FIG. 5, especially an X-ray diffraction diagram identical to that shown in FIG. 5.

The invention expressly relates also to those forms of the methanesulfonic acid addition salt of a compound of formula I in which crystals of the F-crystal form, G-crystal form, H-crystal form, I-crystal form and K-crystal form are present along with other crystal forms, in particular the α-crystal form, the β-crystal form, and/or the amorphous form of the Imatinib mesylate. Preferred, however, is the essentially pure form in the F-crystal form, G-crystal form, H-crystal form, I-crystal form or K-crystal form.

Particularly special preference is for the crystal forms of the methanesulfonic acid addition salt of a compound of formula I obtainable as described in the Examples.

One utility of the F-crystal form, G-crystal form, H-crystal form, I-crystal form and K-crystal form of the methanesulfonic acid addition salt of a compound of formula I is the use as an intermediate for the preparation of a distinct crystal form of the methanesulfonic acid addition salt of a compound of formula I, especially the β-crystal form. The (preferably essentially pure) β-crystal form is obtainable by a) digesting the F-crystal form, G-crystal form, H-crystal form, I-crystal form or the K-crystal form of the methanesulfonic acid addition salt of a compound of formula I with a suitable polar solvent, especially an alcohol, most especially methanol, or also a ketone (especially in a mixture with water, for example water/acetone), typically acetone, a N,N-di-lower alkyl-lower alkanecarboxamide, typically N,N-dimethylformamide or -acetamide, or a hydrophilic ether, typically dioxane, preferably in the presence of some water, or mixtures thereof, in suspension at a suitable temperature, preferably a temperature between 20 and 50° C., for example at about 25° C., or b) dissolving the F-crystal form, G-crystal form, H-crystal form, I-crystal form or the K-crystal form of the methanesulfonic acid addition salt of a compound of formula I with a suitable polar solvent, such as especially an alcohol, typically methanol or ethanol, a ketone (especially in a mixture with water, for example water/acetone) typically acetone, a N,N-di-lower alkyl-lower alkanecarboxamide, typically N,N-dimethylformamide or -acetamide, or a hydrophilic ether, typically dioxane, or mixtures thereof, preferably in the presence of some water, at a suitable temperature, especially after heating the solvent, or while warming during the dissolution process, in both cases preferably to 25° C. up to the reflux temperature of the reaction mixture, and then initiating crystallisation by adding a small amount of the β-crystal form as seed crystal at a suitable temperature, for example between 0 and 70° C., preferably between 20 and 70° C.

One of the advantages of having access to different crystal forms of the compound of formula I is the fact that distinct crystal forms are prone to incorporate distinct impurities upon crystallization, i.e. an impurity incorporated in crystal form β is not necessarily also incorporated in the F-crystal form, G-crystal form, H-crystal form, I-crystal form or K-crystal form. With other words, preparing consecutively distinct crystal forms of the same material increases the purity of the finally obtained substance. Furthermore, distinct crystal forms display different physical properties such as melting points, hygroscopicities, solubilities, flow properties or thermodynamic stabilities, and, hence, distinct crystal forms allow the choice of the most suitable form for a certain use or aspect, e.g. the use as an intermediate in the process of drug manufacture or in distinct administration forms like tablets, capsules, ointments or solutions.

The F-crystal form, G-crystal form, H-crystal form, I-crystal form and K-crystal form of the methanesulfonic acid addition salt of a compound of formula I possess valuable pharmacological properties and may, for example, be used as an anti-tumour agent or as an agent to treat restenosis.

The present invention relates especially to the F-crystal form, G-crystal form, H-crystal form, I-crystal form and K-crystal form of the methanesulfonic acid addition salt of a compound of formula I in the treatment of one of the said diseases mentioned herein or in the preparation of a pharmacological agent for the treatment thereof.

The antiproliferative, especially anti-tumour, activity of the methanesulfonic acid addition salt of a compound of formula I in vivo is, for example, described for the treatment of abl-dependent tumours in Nature Med. 2, 561-6 (1996).

The invention relates also to a method for the treatment of warm-blooded animals suffering from said diseases, especially leukemia, wherein a quantity of the F-crystal form, G-crystal form, H-crystal form, I-crystal form or K-crystal form of the methanesulfonic acid addition salt of a compound of formula I which is effective against the disease concerned, especially a quantity with antiproliferative efficacy, is administered to warm-blooded animals in need of such treatment. The invention relates moreover to the use of the F-crystal form, G-crystal form, H-crystal form, I-crystal form and K-crystal form of the methanesulfonic acid addition salt of a compound of formula I for the preparation of pharmaceutical compositions for use in treating the human or animal body, especially for the treatment of tumours, such as gliomas or prostate tumours.

In preferred embodiments, the present invention relates to the use in of the F-crystal form, G-crystal form, H-crystal form, I-crystal form and K-crystal form of the methanesulfonic acid addition salt of a compound of formula I in the treatment of one of the disorders listed below:

1. metastatic, inoperable GIST,
2. advanced chronic myeloid leukemia,
3. newly diagnosed chronic myeloid leukemia,
4. pediatric Philadelphia chromosome-positive chronic myeloid leukemia,
5. Philadelphia chromosome-positive acute lymphocytic leukemia (ALL),
6. glioblastoma multiforme, preferably in combination with hydroxyurea,
7. dermatofibrosarcoma protuberans (DFSP),
8. hypereosinophilic sindrome (HES), and
9. chronic myelomonocytic leucemia (CMML).

Depending on species, age, individual condition, mode of administration, and the clinical picture in question, effective doses, for example daily doses of about 50-2500 mg, preferably 100-1000 mg, especially 250-800 mg, of Imatinib having the F-crystal form G-crystal form, H-crystal form, I-crystal form or the K-crystal form, are administered to warm-blooded animals of about 70 kg bodyweight. Preferably, daily dosages of 400 mg or 600 mg are administered orally once daily, preferably together with a meal and a large glass of water (about 200 mL). 800 mg daily dosages are preferably administered in the form of 400 mg dosages twice daily together with food.

The F-crystal form, G-crystal form, H-crystal form, I-crystal form and K-crystal form described herein can be utilized to prepare stable pharmaceutical dosage forms. Hence, the invention relates also to pharmaceutical preparations which contain an amount, especially an effective amount for prevention or treatment of one of the diseases mentioned herein, of the methanesulfonic acid addition salt of a compound of formula I in the F-crystal form, G-crystal form, H-crystal form, I-crystal form or K-crystal form, together with pharmaceutically acceptable carriers which are suitable for topical, enteral, for example oral or rectal, or parenteral administration and may be inorganic or organic and solid or liquid. Especially tablets or gelatin capsules containing the active substance together with diluents, for example lactose, dextrose, sucrose, mannitol, sorbitol, cellulose, and/or glycerin, and/or lubricants, for example silica, talc, stearic acid, or salts thereof, typically magnesium or calcium stearate, and/or polyethylene glycol, are used for oral administration. Tablets may likewise contain binders, for example magnesium aluminium silicate, starches, typically corn, wheat or rice starch, gelatin, methylcellulose, sodium carboxymethylcellulose and/or polyvinylpyrrolidone, and, if so desired, disintegrants, for example starches, agar, alginic acid, or a salt thereof, typically sodium alginate, and/or effervescent mixtures, or adsorbents, colouring agents, flavours, and sweetening agents. The pharmacologically active compounds of the present invention may further be used in the form of preparations for parenteral administration or infusion solutions. Such solutions are preferably isotonic aqueous solutions or suspensions, these possibly being prepared before use, for example in the case of lyophilised preparations containing the active substance either alone or together with a carrier, for example mannitol. The pharmaceutical substances may be sterilised and/or may contain excipients, for example preservatives, stabilisers, wetting agents and/or emulsifiers, solubilisers, salts for the regulation of osmotic pressure, and/or buffers. The present pharmaceutical preparations which, if so desired, may contain further pharmacologically active substances, are prepared in a manner known per se, for example by means of conventional mixing, granulating, coating, dissolving or lyophilising processes, and contain from about 1% to 100%, especially from about 1% to about 20%, of the active substance or substances. In a preferred embodiment, the tablet or capsule contains 50 mg 100 mg of the of the methanesulfonic acid addition salt of a compound of formula I in the F-crystal form, G-crystal form, H-crystal form, I-crystal form or K-crystal form, optionally together with pharmaceutically acceptable carriers.

In one embodiment, the capsule is a hard gelatine capsule containing a dry powder blend. The capsule shell preferably contains gelatine and titanium dioxide as well as red iron oxide. The ratio of weight of capsule fill to capsule shell is preferably between about 100:25 and 100:50, more preferably between 100:30 and 100:40.

In another embodiment, a film coated tablet is used comprising 100 mg, 400 mg or 800 mg drug substance together with inactive excepients selected from colloidal anhydrous silica, polyvinylpyrrolidone, magnesium stearate and microcrystalline cellulose.

The following Examples illustrate the invention without limiting the scope thereof. Temperatures are given in degrees Celsius (° C.).

EXAMPLES

Example 1

Preparation of Crystalline Form F of Imatinib Mesylate Using Benzyl Alcohol

About 500 mg of Imatinib mesylate is first dissolved in about 100 ml of water. About 50 µl of the stock solution is dispensed manually into a CRISSY 96-well block, to have a total amount of drug substance of 5 mg per well. The solution is flushed with nitrogen at room temperature to dry the solution. The dry precipitate is resuspended with 250 µl of benzyl alcohol. The suspension or solution is agitated using High-speed vortexer at about 45-55° C. for about 2 hrs. The solution is then allowed to evaporate at 45° C. to 55° C. under a stream of nitrogen.

Example 2

Preparation of Crystalline Form F of Imatinib Mesylate Using a Mixture of Benzyl Alcohol and Ethyl Acetate About 500 mg of Imatinib mesylate is first dissolved in about 100 ml of water. About 50 µl of the stock solution is dispensed manually into a CRISSY 96-well block, to have a total amount of drug substance of 5 mg per well. The solution is flushed with nitrogen at room temperature to dry the solution. The dry precipitate is resuspended with a mixture of 222 μl of benzyl alcohol and 28 μl of ethyl acetate. The suspension or solution is agitated using High-speed vortexer at about 45-55° C. for about 2 hrs. The solution is then allowed to evaporate at 45° C. to 55° C. under a stream of nitrogen.

Example 3

Preparation of Crystalline Form F of Imatinib Mesylate Using a Mixture of Benzyl Alcohol and 1,4-Dioxane, 3-Pentanone or Diisopropyl Ether About 500 mg of Imatinib mesylate is first dissolved in about 100 ml of water. About 50 μl of the stock solution is dispensed manually into a CRISSY 96-well block, to have a total amount of drug substance of 5 mg per well. The solution is flushed with nitrogen at room temperature to dry the solution. The dry precipitate is resuspended with a mixture of 214 μl of benzyl alcohol and 36 μl of 1,4-dioxane, 3-pentanone or diisopropyl ether. The suspension or solution is agitated using High-speed vortexer at about 45-55° C. for about 2 hrs. The solution is then allowed to evaporate at 45° C. to 55° C. under a stream of nitrogen. The crystals obtained from the mixture consisting of benzyl alcohol/diisopropyl ether. A DSC curve (recorded using a Perkin Elmer DSC-7 instrument with a heating rate of 10K/min and a sample mass of about 0.7 mg) shows a melting event at 95° C. followed by an exothermic recrystallization and a second melting at about 223° C.

Example 4

Preparation of Crystalline Form F of Imatinib Mesylate Using a Mixture of Benzyl Alcohol and Acetonitrile or Dimethyl Formamide About 500 mg of Imatinib mesylate is first dissolved in about 100 ml of water. About 50 μl of the stock solution is dispensed manually into a CRISSY 96-well block, to have a total amount of drug substance of 5 mg per well. The solution is flushed with nitrogen at room temperature to dry the solution. The dry precipitate is resuspended with a mixture of 200 μl of benzyl alcohol and 50 μl of acetonitrile or dimethyl formamide. The suspension or solution is agitated using High-speed vortexer at about 45-55° C. for about 2 hrs. The solution is then allowed to evaporate at 45° C. to 55° C. under a stream of nitrogen.

Example 5

Tablets with Imatinib Mesylate, F-Crystal Form

Tablets containing 100 mg of the active substance named in the title are usually prepared in the following composition:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).
Avicel is microcrystalline cellulose (FMC, Philadelphia, USA).
PVPPXL is polyvinylpolypyrrolidone, cross-linked (BASF, Germany).
Aerosil is silicon dioxide (Degussa, Germany).

Example 6

Capsules with Imatinib Mesylate, F-Crystal Form

Capsules containing 100 mg of the compound named in the title as active substance are usually prepared in the following composition:

| Composition | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

Example 7

Preparation of Crystalline Form G of Imatinib Mesylate Using a Mixture of 3-Pentanone and Cyclohexane About 500 mg of Imatinib mesylate is first dissolved in about 100 ml of water. About 50 μl of the stock solution is dispensed manually into a CRISSY 96-well block, to have a total amount of drug substance of 5 mg per well. The solution is flushed with nitrogen at room temperature to dry the solution. The dry precipitate is resuspended with a mixture of 125 μl of 3-pentanone and 125 μl of cyclohexane. The suspension or solution is agitated using High-speed vortexer at about 45-55° C. for about 2 hrs. The solution is then allowed to evaporate at 45° C. to 55° C. under a stream of nitrogen.

Example 8

Tablets with Imatinib Mesylate, G-Crystal Form

Tablets containing 100 mg of the active substance named in the title are usually prepared in the following composition:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).

Avicel is microcrystalline cellulose (FMC, Philadelphia, USA).

PVPPXL is polyvinylpolypyrrolidone, cross-linked (BASF, Germany).

Aerosil is silicon dioxide (Degussa, Germany).

Example 9

Capsules with Imatinib Mesylate, G-Crystal Form

Capsules containing 100 mg of the compound named in the title as active substance are usually prepared in the following composition:

| Composition | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

Example 10

Preparation of Crystalline Form H of Imatinib Mesylate Using a Mixture of 3-Pentanone and N,N-Dimethylformamide About 500 mg of Imatinib mesylate is first dissolved in about 100 ml of water. About 50 µl of the stock solution is dispensed manually into a CRISSY 96-well block, to have a total amount of drug substance of 5 mg per well. The solution is flushed with nitrogen at room temperature to dry the solution. The dry precipitate is resuspended with a mixture of 125 µl of 3-pentanone and 125 µl of N,N-dimethylformamide. The suspension or solution is agitated using High-speed vortexer at about 45-55° C. for about 2 hrs. The solution is then allowed to evaporate at 45° C. to 55° C. under a stream of nitrogen.

Example 11

Tablets with Imatinib Mesylate, H-Crystal Form

Tablets containing 100 mg of the active substance named in the title are usually prepared in the following composition:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).

Avicel is microcrystalline cellulose (FMC, Philadelphia, USA).

PVPPXL is polyvinylpolypyrrolidone, cross-linked (BASF, Germany).

Aerosil is silicon dioxide (Degussa, Germany).

Example 12

Capsules with Imatinib Mesylate, H-Crystal Form

Capsules containing 100 mg of the compound named in the title as active substance are usually prepared in the following composition:

| Composition | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

Example 13

Preparation of Crystalline Form I of Imatinib Mesylate Using a Mixture of Ethyl Acetate and Diethyl Ether About 500 mg of Imatinib mesylate is first dissolved in about 100 ml of water. About 50 µl of the stock solution is dispensed manually into a CRISSY 96-well block, to have a total amount of drug substance of 5 mg per well. The solution is flushed with nitrogen at room temperature to dry the solution. The dry precipitate is resuspended with a mixture of 125 µl of ethyl acetate and 125 µl of diethyl ether. The suspension or solution is agitated using High-speed vortexer at about 45-55° C. for about 2 hrs. The solution is then allowed to evaporate at 45° C. to 55° C. under a stream of nitrogen.

Example 14

Tablets with Imatinib Mesylate, I-Crystal Form

Tablets containing 100 mg of the active substance named in the title are usually prepared in the following composition:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).

Avicel is microcrystalline cellulose (FMC, Philadelphia, USA).

PVPPXL is polyvinylpolypyrrolidone, cross-linked (BASF, Germany).

Aerosil is silicon dioxide (Degussa, Germany).

Example 15

Capsules with Imatinib Mesylate, I-Crystal Form

Capsules containing 100 mg of the compound named in the title as active substance are usually prepared in the following composition:

| Composition | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

Example 16

Preparation of Crystalline Form K of Imatinib Mesylate Using a Mixture of Ethyl Acetate and N,N-Dimethylformamide About 500 mg of Imatinib mesylate is first dissolved in about 100 ml of water. About 50 μl of the stock solution is dispensed manually into a CRISSY 96-well block, to have a total amount of drug substance of 5 mg per well. The solution is flushed with nitrogen at room temperature to dry the solution. The dry precipitate is resuspended with a mixture of 125 μl of 3-ethyl acetate and 125 μl of N,N-dimethylformamide. The suspension or solution is agitated using High-speed vortexer at about 45-55° C. for about 2 hrs. The solution is then allowed to evaporate at 45° C. to 55° C. under a stream of nitrogen.

Example 17

Tablets with Imatinib Mesylate, K-Crystal Form

Tablets containing 100 mg of the active substance named in the title are usually prepared in the following composition:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).

Avicel is microcrystalline cellulose (FMC, Philadelphia, USA).

PVPPXL is polyvinylpolypyrrolidone, cross-linked (BASF, Germany).

Aerosil is silicon dioxide (Degussa, Germany).

Example 18

Capsules with Imatinib Mesylate, K-Crystal Form

Capsules containing 100 mg of the compound named in the title as active substance are usually prepared in the following composition:

| Composition | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

What is claimed is:

1. Crystalline form I of the methanesulfonic acid addition salt of a compound of formula I

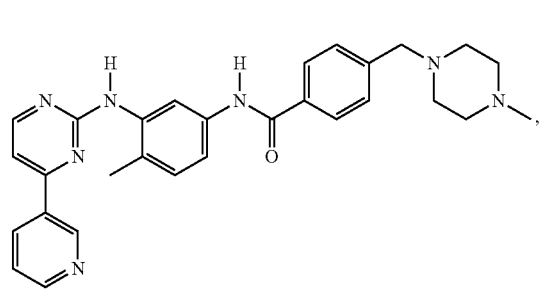

which is characterized by an X-ray diffraction pattern comprising peaks at a diffraction angle 2θ of: 12.9°, 14.1°, 17.1°, 18.0°, 18.7°, 19.1°, 19.8°, 20.9°, 23.9°, 24.3° and 25.2°.

2. The crystalline form according to claim 1, which is characterized by an X-ray diffraction pattern comprising at least a peak at diffraction angle 2θ of 12.9°.

3. The crystalline form according to claim 1, which is characterized by X-ray pattern comprising peaks at diffraction angle 2θ of 12.9°, 17.1°, 20.9°, 23.9° and 24.3°.

4. The crystalline form according to claim 1, which is present in an amount of at least 90 percent by weight, based on the weight of the compound of formula I.

5. A pharmaceutical composition comprising crystalline form I of the methanesulfonic acid addition salt of a compound of formula I

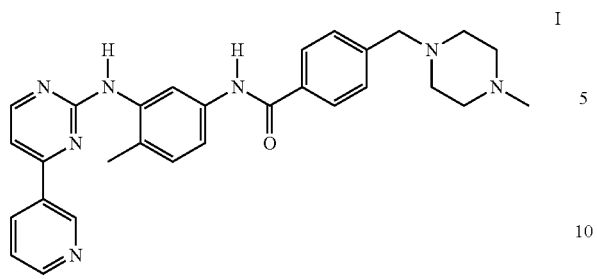

which is characterized by an X-ray diffraction pattern comprising peaks at a diffraction angle 2θ of 12.9°, 14.1°, 17.1°, 18.0°, 18.7°, 19.1°, 19.8°, 20.9°, 23.9°, 24.3° and 25.2°, together with a pharmaceutically acceptable carrier.

6. The pharmaceutical composition according to claim 5 comprising between 50 mg and 800 mg of crystalline form I of the methanesulfonic acid addition salt of a compound of formula I.

7. The pharmaceutical composition according to claim 5 which is a capsule containing a dry powder blend comprising between 50 mg and 200 mg of crystalline form I of the methanesulfonic acid addition salt of a compound of formula I.

* * * * *